United States Patent [19]

Roling

[11] Patent Number: 4,673,489

[45] Date of Patent: Jun. 16, 1987

[54] METHOD FOR PREVENTION OF FOULING IN A BASIC SOLUTION BY ADDITION OF SPECIFIC NITROGEN COMPOUNDS

[75] Inventor: Paul V. Roling, Spring, Tex.

[73] Assignee: Betz Laboratories, Inc., Trevose, Pa.

[21] Appl. No.: 786,274

[22] Filed: Oct. 10, 1985

[51] Int. Cl.$^4$ .......................... C10G 9/12; C10G 9/16
[52] U.S. Cl. ............................... 208/289; 208/48 AA; 208/48 R; 585/800; 585/950; 423/245; 423/228
[58] Field of Search ................ 208/48 AA, 48 R, 289; 585/950, 800; 423/245, 228

[56] References Cited

U.S. PATENT DOCUMENTS

| | | | |
|---|---|---|---|
| 2,568,583 | 9/1951 | Graves | 208/289 |
| 3,281,489 | 10/1966 | Goering | 585/262 |
| 3,291,795 | 12/1966 | Whiton et al. | 585/950 |
| 3,336,414 | 8/1967 | Woerner | 585/800 |
| 3,340,160 | 9/1967 | Waldby | 208/48 AA |
| 3,535,399 | 10/1970 | Tabler | 585/854 |
| 3,617,479 | 11/1971 | King, Jr. | 585/950 |
| 3,631,123 | 12/1971 | Becker | 585/854 |
| 3,645,886 | 2/1972 | Gillespie et al. | 208/48 AA |
| 3,793,187 | 2/1974 | Marx et al. | 208/48 AA |
| 3,801,669 | 4/1974 | Christmann | 585/658 |
| 4,405,825 | 9/1983 | Fenton et al. | 208/289 |
| 4,409,408 | 10/1983 | Miller | 585/950 |
| 4,434,307 | 2/1984 | Miller | 585/950 |
| 4,456,526 | 6/1984 | Miller et al. | 208/48 AA |
| 4,466,946 | 8/1984 | Goddin, Jr. et al. | 208/289 |
| 4,469,586 | 9/1984 | Ferm | 208/48 AA |
| 4,551,226 | 11/1985 | Ferm | 208/48 AA |
| 4,556,476 | 12/1985 | Miller et al. | 585/950 |
| 4,575,455 | 3/1986 | Miller | 423/228 |

FOREIGN PATENT DOCUMENTS 1662698 5/1974 U.S.S.R. .................... 208/48 AA

*Primary Examiner*—Andrew H. Metz
*Assistant Examiner*—Helane Myers
*Attorney, Agent, or Firm*—Alexander D. Ricci; Bruce E. Peacock; James D. Dee

[57] ABSTRACT

The present invention is directed to the use of hydroxylamine, its acid salts or mixtures thereof to prevent fouling during the basic washing of hydrocarbons containing oxygenated compounds. More specifically, oxygenated compounds such as carbonyl containing organics have a tendency to polymerize, producing fouling elements when such are contained in hydrocarbons being washed with basic materials. The hydroxylamine and its salts are quite effective in reducing the fouling tendencies due to these specific mechanisms.

18 Claims, No Drawings

METHOD FOR PREVENTION OF FOULING IN A BASIC SOLUTION BY ADDITION OF SPECIFIC NITROGEN COMPOUNDS

BACKGROUND OF THE INVENTION

This invention relates to the prevention of fouling in a basic solution which is in contact with a gaseous or liquid hydrocarbon stream.

In cracking operations (pyrolysis) such as in the cracking (pyrolysis) of ethane, propane, and naphthas to olefins, oxygenated compounds, including carbonyl compounds, are formed. The amount of carbonyl compounds, such as aldehydes and ketones, formed in such an operation can vary widely, but is typically about 1–100 ppm in the gas stream with concentrations as high as 1000 ppm occasionally being encountered because of the utilization of the various feedstocks and cracking temperatures. When the gas stream is passed through a basic wash (pH>7) to remove acidic components such as hydrogen sulfide and carbon dioxide, oxygenated compounds and carbonyl compounds are also removed. These oxygen compounds, particularly acetaldehyde, will undergo polymerization in the presence of the base. In the wash tower, the polymer will settle on the trays leading to fouling and eventual plugging of the trays, which means the unit must be shut down to clean the trays—obviously a costly operation. The type basic wash systems where treatment is required to inhibit fouling include amine acid gas scrubber (e.g., MEA, DEA, isopropyl amine, butyl amine, etc.) and caustic wash systems.

Prior Art

U.S. Pat. Nos. 3,336,414 and 3,308,201 disclose processes utilizing aqueous caustic washes (pH>10) of carbonyl-contaminated hydrocarbons to remove carbonyl compounds.

In U.S. Pat. No. 3,281,489, carbonyl compounds, aldehydes, are removed from a butadiene stream (obtained from the pyrolysis of saturated hydrocarbons) by selective hydrogenation to reduce some of the carbonyls. This procedure is followed by caustic washing to remove substantially all of the remaining carbonyl compounds. If caustic washing is performed before the hydrogenation, carbonyl polymeric materials from Aldol condensation foul the process equipment. U.S. Pat. No. 3,801,669 discloses the use of Portland cement to extract carbonyl compounds from hydrocarbon streams.

At acid pH, extraction of carbonyl compounds from hydrocarbon streams by aqueous solutions of hydrazine compounds is reported in U.S. Pat. No. 3,793,187. The carbonyl compounds need to be extracted because they have an inhibiting effect on further processing steps. Only extractions of liquid systems are contemplated in this patent.

In U.S. Pat. No. 3,535,399, carbonyl compounds are removed from gaseous hydrocarbon streams by contacting the streams with an aqueous solution of sodium hydroxide and urea. The caustic removes acid materials and the urea complexes with the carbonyl compounds to form aldehyde-urea or ketone-urea resins that are reportedly entrained in the aqueous solution.

Substituted hydroxylamine compounds such as N,N-diethylhydroxylamine are used to prevent polymerization of unsaturated aldehydes in dilute alcohol solutions, but not of the neat unsaturated aldehydes in U.S. Pat. No. 3,849,498.

German Pat. No. 1,072,607 discloses that polystyrene based cation exchange resins can be treated with a solution of hydroxlyamine hydrochloride to remove carbonyl compounds from sulfite liquor.

French Pat. No. 1,546,472 discloses a procedure of treating a carbonyl-contaminated glycerol with an acid and 2,4-dinitro-phenyl hydrazine.

GENERAL DESCRIPTION OF THE INVENTION

After reviewing the problems associated with carbonyl contamination of hydrocarbons, particularly the gaseous olefins derived from pyrolytic cracking, it was apparent to the present inventor that the cracking industry required a treatment which would control the formation and deposition of fouling materials during the basic wash of hydrocarbons. Most desirably, the treatment would be such that it would operate effectively in the highly basic wash to alleviate the potential problems due to the oxygenated compounds, particularly the carbonyls without the formation of other solid materials which had to be removed. The treatment not only had to be effective but also cost-effective.

The present inventor discovered a method of inhibiting the formation and deposition of fouling materials during the basic wash and in particular the caustic wash of hydrocarbons containing oxygenated compounds, and in particular the gaseous olefins containing carbonyl compounds. The latter carbonyl compounds under alkaline conditions undergo in many instances Aldol condensation reactions to produce polymeric materials which deposit on the equipment and in particular plug the trays in the caustic wash tower.

The inventive method is particularly appropriate for the basic washing process which follows the pyrolytic cracking of such hydrocarbons as ethane, propane, butane, naphtha and mixtures thereof to produce the corresponding gaseous ethylene, propylene, butadiene and the like, containing the carbonyl as well as other contaminants.

Generally the basic washing entails contacting in wash towers an aqueous basic solution with the gaseous olefins to remove any hydrogen sulfide, carbon dioxide and other oxygenated compounds. As earlier discussed the conditions are such as to be conducive for condensation reactions of any aldehydes/ketones (acetaldehydes) contained therein.

The method entails assuring that the basic wash takes place in the presence of the hydroxylamine compounds thereof.

Details of Invention

The hydroxylamine compounds of the invention can be used in the form of their hydrates, or salts wherein said salt is derived from a mineral acid such as sulfuric acid, hydrochloric acid, nitric acid, etc., or salts wherein said salt is derived from an organic acid such as acetic acid, propanoic acid, and the like. The acid portions of the salts will be neutralized by the base of the system and since only small portions of the acid salts are to be used, very little of the base will be used in the neutralization.

These fouling inhibitors can be added to the caustic tower as neat materials or as solutions. The preferred method of addition is as an aqueous solution with 2 to 50 weight percent inhibitor present, so that accurate metering of the inhibitor to the tower can be achieved. The fouling inhibitors can be used in a continuous or batch process.

It is theorized that the inhibitors prevent fouling by forming a complex with the carbonyl compounds and that the complex does not undergo polymerization. For one mole of carbonyl compound, one mole of inhibitor is needed. However, since other unknown side reactions could consume the inhibitor, a molar ratio greater than 1:1 should be used. In general, a molar ratio of 1:1 to 10:1 of inhibitor to carbonyl content should suffice, with a preferred ratio of 1:1 to 3:1.

A preferred formulation of the hydroxylamine for addition to the basic wash would on a weight basis comprise 12% hydroxylamine or its chloride or sulfate salts
88% water.

This product would be added to the wash in quantities to assure that the molar ratio of hydroxylamine to oxygenated or carbonyl compound is 1:1 or greater. Treatment ranges of from about 1 to 10,000 parts of product per million of wash solution could be utilized.

Experimental

The following examples are given to illustrate the invention, but are not meant to be limiting. The test conditions in the examples are accelerated conditions to show the effects of the inhibitors in a short period of time instead of in the three months or more of the field conditions.

Examples with letter designations are comparative examples, while numbered examples exemplify the present invention.

EXAMPLE A

Into a round-bottomed flask equipped with a magnetic stirrer and a reflux condenser, there were introduced 95 mL of water and 5 g (0.11 mol) of acetaldehyde. This mixture was refluxed for one hour. At the end of this period no polymer was observed.

EXAMPLE B

Example A was repeated but the water was made to a pH of 3.5 by addition of hydrochloric acid. Again at the end of one hour no polymer was noted.

EXAMPLE C

As in Example A, there was refluxed 5 g (0.125 mol) of sodium hydroxide, 90 mL of water, and 5 g of acetaldehyde for one hour. An orange solution and polymer resulted. The polymer was filtered, air-dried, and weighed. The polymer weighed 3.7 g. In three other runs there resulted 4 g, 5 g, and 2 g of polymer.

In the above three comparative examples, it is shown that under neutral (Example A) or acid (Example B) conditions the polymer did not form. Therefore, use of prior art treatments such as the hydrazine extraction of carbonyl compounds is not obvious for treatment under the basic conditions of the present invention. However, under the caustic conditions of Example C, a large amount of polymer resulted.

EXAMPLE D

As in Example A, 5 g of sodium hydroxide, 7 g (0.12 mol) of urea, 83 mL of water and 5 g of acetaldehyde were refluxed for one hour. There resulted 1.5 g of polymer.

EXAMPLE E

As in Example A, 5 g of sodium hydroxide, 10 g (0.12 mol) of N,N-diethylhydroxylamine, 80 mL of water and 5 g of acetaldehyde were refluxed for one hour. The resulting polymer weighed 4 g.

EXAMPLE F

As in Example A, 5 g of sodium hydroxide, 7 g (0.12 mol) of monoethanolamine, 83 mL of water and 5 g of acetaldehyde were refluxed for one hour. The polymer that resulted weighed 1 g.

The Examples D, E, and F show that the prior art methods of urea (Example D) and of substituted hydroxylamines (Example E) and that other amines do not prevent polymer formation under the basic conditions.

EXAMPLE G

As in Example A, 5 g of sodium hydroxide, 13 g (0.12 mol) of hydroquinone, 77 mL of water and 5 g of acetaldehyde were refluxed for one hour. There resulted 7.5 g of polymer. This example shows that the polymer formation is not inhibited by traditional antioxidant scavenger-reducing compounds.

EXAMPLE H

Refluxed for 1 hour, 5.0 g of sodium hydroxide, 5.0 g of acetaldehyde (0.11 mol), 80 mL of water, 10 mL of a 30 wt % aqueous solution of hydroxylamine sulfate (0.03 mol). There resulted 3.0 g of a solid and the solution was dark red in color. This example shows that, at a less than stoichiometric ratio of 1:1 of hydroxylamine to carbonyl, fouling still occurs.

EXAMPLE I

Twenty mL of monoethanolamine (MEA), 75 mL of water, and 5 g of acetaldehyde were refluxed for one hour. At the end of this time, the solution was deep red and small amounts of a polymer were on the sides of the flask. This example shows that fouling can occur with bases other than caustic.

EXAMPLE 1

As in Example A, 9.5 g of sodium hydroxide (the extra 4.5 g were added to neutralize the acid from the hydroxylamine), 8 g (0.12 mol) of hydroxylamine hydrochloride, 77.5 mL of water and 5 g of acetaldehyde were refluxed one hour. At the end of the reflux period, the solution was virtually colorless and no polymer had formed. A second reaction was conducted with the same result.

EXAMPLE 2

Refluxed for 1 hour, 8.0 g of sodium hydroxide, 5.0 g of acetaldehyde, 55 mL of water, and 35 mL of a 30 wt % aqueous solution of hydroxylamine sulfate [$(NH_2OH)_2H_2SO_4$)] (0.12 mol). There resulted a colorless solution with no polymer.

EXAMPLE 3

As in Example I, 20 mL of MEA, 45 mL of water, 5 g of acetaldehyde, and 35 mL of a 30 wt % aqueous solution of hydroxylamine sulfate were refluxed for one hour. At the end of this time, the solution was clear with a slight yellow tinge and no polymer had formed.

Examples 1, 2, and 3 illustrate the efficacy of the invention.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What I claim is:

1. A method for inhibiting the formation and deposition of fouling materials during the basic washing of hydrocarbons contaminated with oxygenated compounds which comprises performing the wash of the hydrocarbon in the presence of sufficient amount for inhibiting the formation and deposition of fouling of hydroxylamine, of the formula $NH_2OH$ or an acid salt or mixtures thereof.

2. A method according to claim 1 wherein the hydrocarbon being washed is produced by the pyrolytic cracking of other hydrocarbons.

3. A method according to claim 2 wherein said other hydrocarbon is ethane, propane, butane, naphtha or mixtures thereof.

4. A method according to claim 3 wherein the hydrocarbon being washed contains an olefin contaminated with oxygenated compound impurities.

5. A method according to claim 4 wherein the hydrocarbon being washed is in a gaseous state.

6. A method according to claim 5 wherein the oxygenated compounds are comprised primarily of carbonyl compounds which would polymerize to produce the fouling materials under the basic conditions of the wash.

7. A method according to claim 6 wherein the carbonyl compounds are aldehydes, ketones or mixtures thereof.

8. A method according to claims 6 or 7 wherein the hydroxylamine or acid salt thereof is added to the basic wash in an amount representing a molar ratio of said hydroxylamine or acid salt thereof to said carbonyl of from about 1:1 to 10:1.

9. A method according to claim 8 wherein the molar ratio is 1:1.

10. A method according to claim 8 wherein the ratio is 1:1 to 3:1.

11. A method of inhibiting the formation and deposition of fouling materials on the structural parts of basic wash equipment during the basic wash of pyrolytically produced olefin contaminated with at least one carbonyl compound, which comprises adding to said wash during said basic wash of said olefin a sufficient amount for inhibiting the formation and deposition of fouling of hydroxylamine, of the formula $NH_2OH$ acidic salt thereof, or a mixture thereof.

12. A method according to claim 11 wherein said olefin with carbonyl compounds is in a gaseous state.

13. A method according to claim 12 wherein said carbonyl compound is an aldehyde, ketone or mixture thereof.

14. A method according to claim 13 wherein said hydroxylamine or acid salt thereof is present in an amount which represents a molar ratio of such to the carbonyl compound of from about 1:1 to 10:1.

15. A method according to claim 14 wherein the molar ratio is from about 1:1 to 3:1.

16. A method according to claim 12, 13 or 14 wherein the hydroxylamine is an acid salt form or is hydroxylamine sulfate.

17. A method according to claim 12, 13 or 14 wherein the hydroxylamine is in salt form and is hydroxylamine chloride.

18. A method according to claim 12, 13 or 14 wherein hydroxylamine is added to said caustic wash.

* * * * *